US005688519A

United States Patent [19]
Leonard

[11] Patent Number: 5,688,519
[45] Date of Patent: Nov. 18, 1997

[54] FLASH-FLOW FUSED MEDICINAL IMPLANTS

[76] Inventor: Robert J. Leonard, 4 Hutchins Cir., Lynnfield, Mass. 01940

[21] Appl. No.: 348,351

[22] Filed: Nov. 28, 1994

Related U.S. Application Data

[63] Continuation of Ser. No. 218,154, Mar. 25, 1994, abandoned, which is a continuation of Ser. No. 82,155, Jun. 24, 1993, abandoned, which is a continuation of Ser. No. 475,200, Feb. 5, 1990, abandoned, which is a continuation of Ser. No. 175,533, Mar. 31, 1988, abandoned, which is a continuation-in-part of Ser. No. 35,379, Apr. 6, 1987, Pat. No. 4,748,024.

[51] Int. Cl.$^6$ ........................................ A61K 31/56
[52] U.S. Cl. ........................ 424/426; 424/502; 514/178
[58] Field of Search ............................ 424/422, 489, 424/502, 423, 426; 514/178

[56] References Cited

U.S. PATENT DOCUMENTS

| | | | |
|---|---|---|---|
| 3,800,038 | 3/1974 | Rudel | 424/433 |
| 4,164,560 | 8/1979 | Folkman et al. | 424/22 |
| 4,244,944 | 1/1981 | Gupta | 514/178 |
| 4,244,949 | 1/1981 | Gupta | 424/243 |
| 4,267,169 | 5/1981 | Kamishita et al. | 424/78 |
| 4,335,097 | 6/1982 | David et al. | 424/433 |
| 4,349,530 | 9/1982 | Boyer | 424/19 |
| 4,391,797 | 7/1983 | Folkman et al. | 424/19 |
| 4,396,630 | 8/1983 | Riedl et al. | 424/365 |
| 4,432,964 | 2/1984 | Shell et al. | 424/14 |
| 4,451,460 | 5/1984 | Hansen et al. | 424/238 |
| 4,452,775 | 6/1984 | Kent | 424/19 |
| 4,526,938 | 7/1985 | Churchill et al. | 525/415 |
| 4,591,496 | 5/1986 | Cohen et al. | 424/15 |
| 4,659,693 | 4/1987 | Nestor | 514/12 |
| 4,667,014 | 5/1987 | Nestor, Jr. et al. | 530/313 |
| 4,686,283 | 8/1987 | Nestor, Jr. et al. | 530/327 |
| 4,690,916 | 9/1987 | Nestor, Jr. et al. | 514/15 |
| 4,748,024 | 5/1988 | Leonard | 424/489 |
| 4,801,577 | 1/1989 | Nestor, Jr. et al. | 514/15 |
| 4,803,076 | 2/1989 | Ranade | 424/438 |
| 4,863,736 | 9/1989 | Azain et al. | 424/423 |
| 4,892,734 | 1/1990 | Leonard | 424/422 |
| 4,894,231 | 1/1990 | Moreau et al. | 424/426 |
| 5,035,891 | 7/1991 | Runkel et al. | 424/423 |
| 5,091,540 | 2/1992 | Molinari | 548/341 |
| 5,110,595 | 5/1992 | Wang | 424/422 |
| 5,132,315 | 7/1992 | Kohn et al. | 514/359 |
| 5,137,669 | 8/1992 | Leonard et al. | 264/120 |
| 5,208,032 | 5/1993 | Scanes et al. | 424/422 |

FOREIGN PATENT DOCUMENTS

| | | | |
|---|---|---|---|
| 3400106 | 7/1985 | Germany | 424/433 |
| 3400106A1 | 11/1985 | Germany . | |
| 2034182 | 4/1980 | United Kingdom . | |
| 2034182 | 6/1980 | United Kingdom | 424/433 |

OTHER PUBLICATIONS

Heller, J. Chapter 3, Bioerodible Systems, vol. 1, pp. 69–101.

*Primary Examiner*—Amy Hulina
*Attorney, Agent, or Firm*—Wolf, Greenfield & Sacks, P.C.

[57] ABSTRACT

A totally-fused pellet and a process and a device for preparing the totally-fused pellet are provided. Conditions are applied to the pelleting material to melt the material uniformly such that the phase transition of all of the material occurs approximately simultaneously. The material is removed from the melting conditions immediately upon the melting of the material and the material is subjected immediately to cooling conditions. The resulting totally-fused pellet contains no thermal degradation impurities.

24 Claims, 8 Drawing Sheets

FLASH-FLOW FUSED MEDICINAL IMPLANTS

RELATED APPLICATION

This application is a file wrapper continuation of application Ser. No. 08/218,154, filed Mar. 25, 1994, now abandoned, which is a continuation of prior application Ser. No. 08/082,155, filed on Jun. 24, 1993, now abandoned, which in turn is a continuation of Ser. No. 07/475,200, filed on Feb. 5, 1990, now abandoned, which is a continuation of application Ser. No. 07/175,533, filed Mar. 31, 1988, now abandoned which is a C-I-P of Ser. No. 07/035,379, filed Apr. 6, 1987, now U.S. Pat. No. 4,748,024.

BACKGROUND OF THE INVENTION

This invention relates in general to fused medicinal implants and to a process for making fused medicinal implants, preferably in the form of cylindrical pellets for the subcutaneous implantation and delivery of drugs. This invention relates in particular to a fused implant and to a process for making a fused implant for fertility control and certain endocrinologically mediated disorders.

It has become widely acknowledged that standard oral and parenteral (intravenous or intramuscular) forms of drug delivery represent relatively inefficient means of administering therapeutic pharmaceuticals, due to considerable drawbacks associated with conventional drug-delivery methods. These drawbacks arise from the way in which standard dosage forms of pharmacologically active compounds are absorbed into the body, circulated through the blood stream, cleared and excreted. Conventional routes of administration generally require the administration of far more of a drug than is therapeutically warranted so that there will be adequate blood levels of drug between doses ("spiking"). Moreover, there are many therapeutically vital substances which present a narrow ratio of efficacy to toxicity that do not, therefore, lend themselves to traditional routes of administration. Additionally, drugs that require daily compliance with a multiple-dose regimen on the part of the patient pose a major problem in the management of the chronically ill, elderly, those with emotional disorders, and people whose lifestyles do not comfortably accommodate regular routine. The lists of conditions requiring such regimens is extensive and includes: diabetes; psychiatric diseases; cancer; and coronary artery disease, to name only a few.

In recent years, various types of novel sustained release drug-delivery systems have begun to receive widespread attention. Such drug-delivery systems include certain implantable devices which slowly dissolve or somehow release drugs while under the patient's skin. Implants are particularly effective and economical forms of treatment because a single administration of such a product can deliver, over a long period of time (a year or more), adequate therapeutic serum levels of a drug without reliance on patient compliance, frequent clinic visits and while avoiding over medication due to "spiking". Known implantable systems have drawbacks. Some are not long-acting enough; some have what are called poor kinetics, which cause them to release drug in less even and predictable amounts over time; some are too long in duration; some are irreversible (impossible to discontinue, once begun); and others require surgical removal when the system is depleted of drug.

Implantable systems for fertility control, as well as for other clinical applications, have long been sought as an alternative to oral preparations of steroids. This approach is particularly attractive to developing nations, where national health-care networks are at a disadvantage in reaching a population which is demographically and educationally ill-controlled. Moreover, significant potential health problems associated with the use of certain steroids have raised many questions as to the wisdom of prescribing steroids in the amounts required for effective oral delivery. A progestogen—only implant for fertility control, the Silastic implant—NORPLANT®—has been extremely well accepted in fertility control trials throughout the world despite the cumbersome nature of multiple, one-inch or longer rods that must be surgically implanted and removed when depleted. The subject of the current invention includes a process which yields a bioerodable fused pellet coupling active and nonactive ingredients and prepared for subdermal implantation, which reduces the disadvantages of the known long-term implantable drug-delivery systems.

It is known that bioabsorbable implants can be made by various methods and utilizing various materials. Several methods have been practiced with steroid drugs. For example, a bioabsorbable implant can be made by tightly compressing powdered steroid. An improved implant results from compressing a combination of a nonactive biocompatible binder and the steroid into a pellet which pellet releases steroid more slowly and more uniformly than the pure steroid pellets.

An important improvement over the compression process for making pellets which results in even longer and more constant dissolution rates, is a method of melting a drug together with a sufficient amount of a nonactive lipoid carrier resulting, when cooled, in a "fused" pellet. The superior kinetics and release rates are believed to be due to the final integral crystal lattice produced from the starting materials.

It has been suggested that a fused implant of a sex steroid uniformly dispersed with a suitable lipoid carrier may provide a convenient, safe and effective form of long-term fertility control in mammals. Specifically, a precise intimate mixture of the starting materials in their micronized or crystalline form, as supplied by the manufacturer, is heated according to the published melting points of either the active ingredient or the carrier or to a eutectic point of the two where a phase change occurs and an isotropic liquid (perfectly clear melt) is achieved. At this point, the materials are allowed to cool or are quenched whereupon the melt hardens through recrystallization into the final, integral, fused pellet. Such fused implants, however, have proven unsuitable for a variety of reasons, largely related to the manufacturing processes used which are not easily reproducible. The background of such fused implants is discussed in greater detail in U.S. Pat. No. 4,244,949 (Gupta).

The methods suggested by Gupta and others for making such a fused implant rely heavily upon manual skills, have a very low yield of effective final product when performed by anyone unpracticed in the procedure and do not lend themselves to automated mass production techniques. In particular, the best of the prior art methods known requires pre-measuring and dispensing into very small vessels minute amounts of active ingredient and carrier. The material must be gradually heated within a vessel while gently applying a continuous pressure, with steel rods, at each end of the vessel until a clear liquid phase is determined by eye. Then the melted material is removed from the heat source and allowed to cool. This human-dependent process not only is inefficient, but is more a craft than a practicable method capable of being reproduced consistently. This is especially important as it relates to the Good Manufacturing Practices promulgated by the FDA as necessary for the commercial approval of any drug.

The requirement of delicate manipulations and skilled judgment on the part of an individual introduces a potential for error with the making of each pellet. The duration of which the material is exposed to temperature is not adequately controlled according to prior art methods and the material may be overheated, causing de-ethynylation of the active ingredient and formation of other impurities. This effect has been misunderstood in previous art resulting in the presumption that oxidation—an atmospheric effect—was the cause of degradation of the final product. Therefore, this art sought to avoid open air or atmosphere melts and introduced manufacturing steps that actually created a greater likelihood of both degradation due to duration of heat exposure as well as the "capturing" of gases within the final product. Moreover, cumbersome procedural steps and apparatus were introduced to avoid open air melts.

The pressure applied to the melt also is not quantitatively controlled according to these prior art methods. Also, the integrity of the final crystal of the fused pellet may be adversely affected by transverse fractures and friability as the crystal forms when the melt is manually removed from the heat source.

Pre-measuring and dispensing of the ingredients by hand into the vessels introduces the potential for error and contamination. Moreover, this practice necessitates an undesirable degree of human exposure to steroids in powder form, demanding the strictest controls according to the rules promulgated by the FDA. Also, certain of the prior art methods require purification of the starting materials by recrystallizing them using various solvents, nitrogen chambers and dessicators in order to assure that gases or moisture were eliminated from the crystals.

The invention overcomes these and other shortcomings. A process is provided for forming a fused pellet that does not require the skilled manipulation and human judgment previously enumerated and that is capable of automation and suitable for large-scale commercial production. Also provided is a process for forming a fused implant that does not result in de-ethynylation or other degradation products of the starting materials. The process for forming a fused pellet further does not require an oxygen-free environment and does not "trap" air or gases, but rather allows the free evaporation of impurities which otherwise might be collected within the tortuous geometry of the individual crystals of the starting materials.

An object of the invention is to provide a fused pellet that does not contain thermal degradation impurities or other impurities, which pellet is capable of delivering asteroid drug in pharmaceutical doses for prolonged periods of time.

A more particular object of the invention is to provide a fused pellet capable of delivering a pharmaceutical dose of an antifertility drug such as norethindrone for periods of a year or more, which pellet is free of impurities resulting from de-ethynylation of norethindrone and is free of other impurities, including those resulting from thermal-degradation of the other starting materials.

Another object of the invention is to provide a process for dispensing the intimate mixture in precise relative amounts in an automated fashion where the active ingredient comprises over 50% of the final drug product.

SUMMARY OF THE INVENTION

A totally-fused pellet capable of sustained release of a drug may be made according to the process of the invention.

The totally-fused pellet may consist entirely of a melted and recrystallized steroid drug. The totally-fused pellet of the invention also may include a lipoid carrier such as, for example, a sterol, cholesterol, or a cholesteric ester. The steroid drug and carrier are melted and recrystallized to form a totally-fused matrix of the steroid drug and carrier. The resulting pellet is characterized by the absence of thermal degradation impurities and other impurities, which impurities occur in pellets made under conditions characteristic of the processes of the prior art. The resulting pellets are also stronger and less friable than those of predecessor processes, and therefore are less likely to break before or after implantation.

In one significant case, the fused pellet is made of an antifertility steroid molecule such as norethindrone (NET) and a lipoid carrier such as pure cholesterol. The pellet is characterized by the absence of the thermal degradation impurities. In particular, the white pellet is characterized by the absence of impurities caused by de-ethynylation of norethindrone. The pellet remains pure even after autoclaving. The pellet further is characterized by a tensile strength of about 0.1 kilogram/mm$^3$ and by a break surface that reveals under electron microscopy the absence of discrete particles—indicating that a total melt and total fusion has occurred. This pellet is capable of releasing norethindrone at an even, continuous level when implanted. Such a fused pellet may be used as an implant for fertility control in humans and animals.

Other applications may include a variety of other drugs for the management of various clinical conditions.

The process of the invention involves applying conditions to a mixture of the starting materials to melt the mixture uniformly such that the phase transition of virtually all of the material occurs simultaneously, preferably over a range of not more than about 10 seconds. The material is then motivated from the heat source, preferably through a combination of the inherent properties of the clear melt and a mechanical force, such as a slight vacuum. The material is allowed to cool, recrystallizing to form a fused pellet.

To accomplish a quick and uniform melt, a flash flow method and device are provided. First, a paste may be made from an intimate mixture of the micronized or crystalline form of the starting materials as supplied by the manufacturer, the active ingredient being present in at least an amount of 50% of the total material. A thin layer of this paste then is applied to a nonstick surface, such as a fluorocarbon like Teflon®, which surface, in turn, is affixed to a thin, heat-conductive metallic wall. The thin layer of paste, nonstick surface and heat conductive wall are oriented at an angle, preferably inclined at least about 45° to horizontal. A heat source then is applied to the surface of the heat conductive wall opposite the surface layered with the nonstick surface and paste. The heat is applied uniformly across this entire surface at a temperature sufficient to uniformly melt the layer or "skin" of material such that the phase transition of all of the material occurs approximately simultaneously, and preferably in 10 seconds or less. Upon the phase transition, the isotropic liquid beads upon the nonstick surface and runs off of this inclined surface. The material is collected as it runs off the surface and is allowed to cool into a fused pellet, preferably within a fluorocarbon chamber of appropriate size and shape.

DETAILED DESCRIPTION OF THE DRAWINGS

The invention may be described by way of example with reference to the drawings.

The invention facilitates the formation of a fused pellet containing an active steroid drug and cholesterol in relative amounts of at least 50% steroid. There is no de-ethynylation or other degradation of the starting materials and air is not entrapped in the pellet. To accomplish this, a thin layer or "skin" of a mixture of the starting materials is applied to a thin layer of conductive metal. Preferably the surface upon which the skin is applied is coated with a nonstick material such as Teflon®. When a heat source well above the melting temperature of the starting materials is applied to the conductive metal, the starting materials mixture reaches a clear melt state in less than 10 seconds, beading like mercury and exhibiting excellent flow characteristics when inclined at an angle of about 45° to horizontal. When so inclined, the melted material is motivated to leave the area of the heat source the moment it reaches the clear melt stage. This eliminates the risk of degradation posed by overexposure to heat, which is a persistent problem of the prior art methods for preparing fused pellets. Moreover, since the procedure is atmospheric, there is no capturing of air.

The clear, nondegraded material will flow from the inclined surface and may be collected into a vessel having a nonstick surface of appropriate size and shape for forming a pellet. Collection and pellet formation may be aided by the application of a slight vacuum from beneath the collection vessel utilizing, for example, a Teflon® filter or a Gortex membrane. The collected material further may be drawn from above or below into a pellet forming chamber of appropriate size and shape by a conventional piston beginning with a plunger in the closed position.

The process of the invention is especially adapted for providing an implant useful for fertility control when implanted under the skin in mammals. A preferred embodiment of the product of the invention is a 35 mg. pellet containing cholesterol and norethindrone at a ratio of about 15:85%. The pellet most preferably is approximately 2½ millimeters in diameter by 6 millimeters in length. Such pellets were prepared using a device as described in Example 3.

An accurate dispensing of the starting materials may be achieved by forming a paste made from the powdered mixture of starting materials and a liquid such as ethyl alcohol, which alcohol may be dried out of the starting materials after dispensing, utilizing, for example, a standard vacuum oven. By forming a paste, the material can be dispensed accurately from a standard, automated device such as a micropipetter. The paste may be manufactured to have the flow characteristics of ordinary toothpaste.

The formation of the paste clearly overcomes problems in the prior art. Where drugs such as steroids are concerned, anything but a precise dosage could either be ineffective or harmful to the user. It is believed that standard pharmaceutical dispensing machinery for dispensing powder does not dispense the very small quantities of powder required for the individual pellets of the invention with sufficient accuracy. This is especially true when the active ingredient comprises over 50% of the total pellet volume. Therefore, according to the prior art, the materials must be measured or carefully aliquoted separately for each pellet. By forming a paste, precise relative amounts of steroid and carrier are maintained homogeneously throughout the paste and individual manual measurements are thus obviated. The paste also facilitates forming the thin "skin" of pelleting materials according to the invention.

The liquid agents used to formulate the paste may be ethyl alcohol, diethylether or any volatile organic solvent which can be evaporated completely prior to carrying out the flash flow process and which when combined with the starting materials yield suitable flow characteristics. Diethylether is preferred. The liquid agent should be of a nature that promotes the quick drying of the paste once the paste is applied as a skin. The liquid agent, of course, should not be of a nature which affects the activity of the active agent in the pellet.

Figure 1:
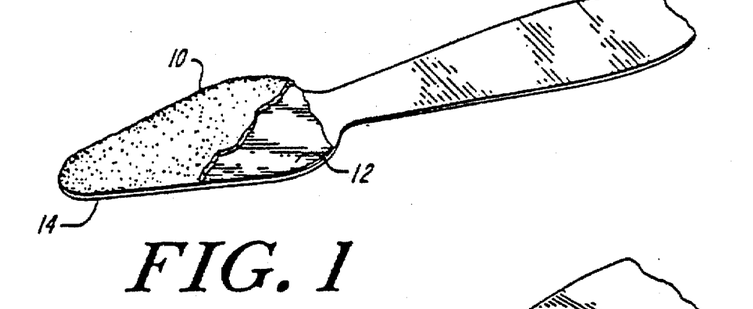
FIG. 1 is a schematic representation showing the material spread in a thin layer prior to fusion.
Figure 2:
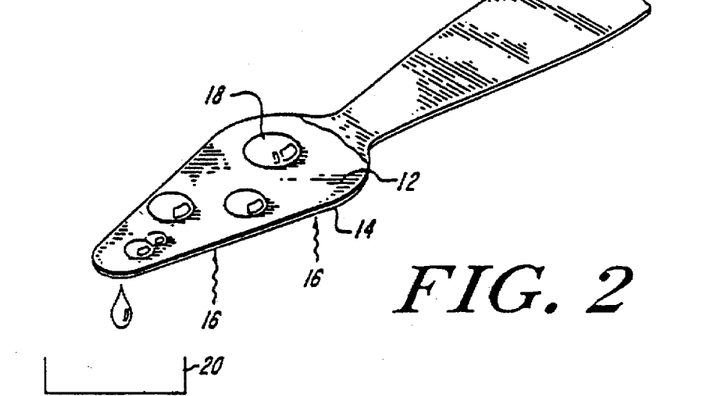
FIG. 2 is a schematic representation showing the material after the application of heat.

FIGS. 1 and 2 are a schematic representation illustrating the basic principles of the flash flow process of the invention. A thin skin 10 of starting materials, less than 1 mm thick, was spread on a Teflon® surface 12 layered on a heat conductive metal base 14. Heat well in excess of the melting temperature of the starting materials, indicated by arrows 16, was then applied to the underside of the heat conductive metal base 14 which was inclined at an angle about 45° to horizontal. In approximately 3 to 5 seconds, the skin 10 melted into a clear liquid 18 which immediately beaded and ran down the Teflon® surface away from the heat source as shown in FIG. 2. The beads of the clear liquid 18 were collected in a vessel 20 away from the heat source. The clear liquid 18 then was allowed to cool.

Figure 3:
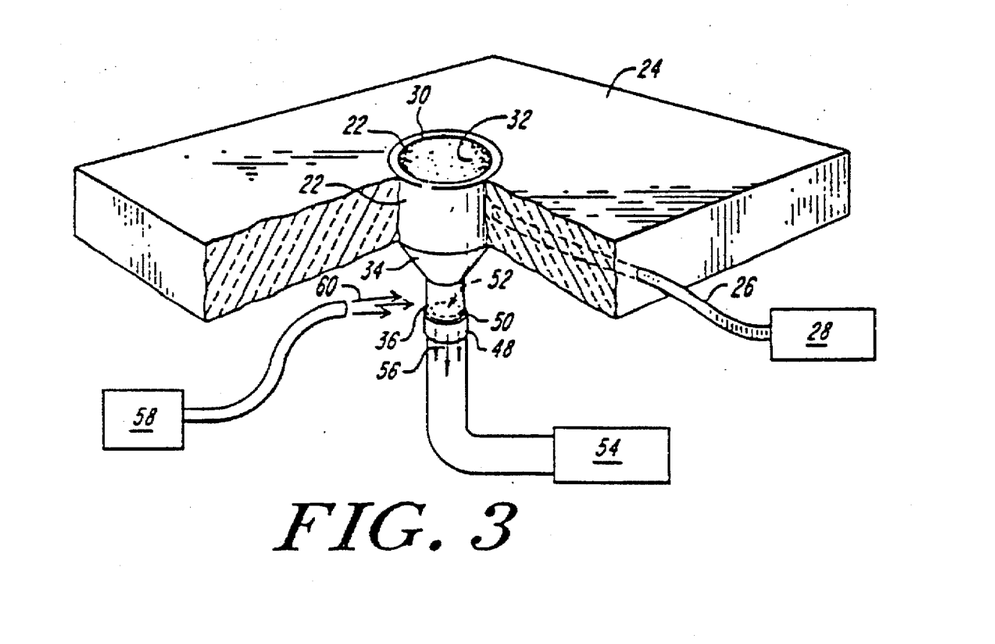
FIG. 3 is a schematic representation showing a device for carrying out the invention.
Figure 4:
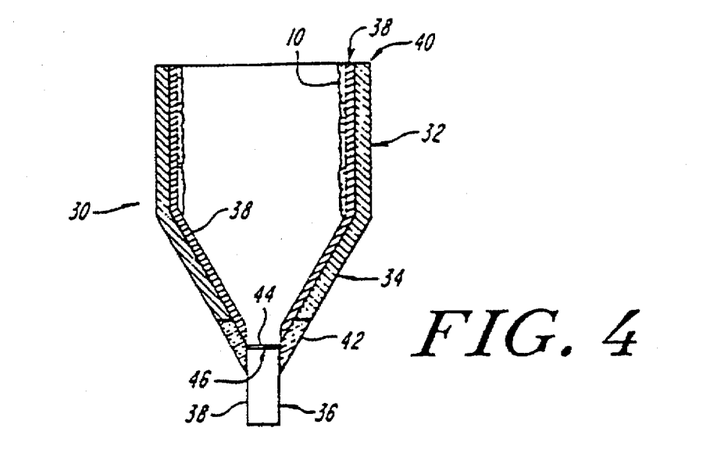
FIG. 4 is a schematic representation of a component device shown in FIG. 3.

FIGS. 3 and 4 illustrate a device for carrying out the flash flow process. A metal heating collar 22 is contained in an insulative ceramic block 24. The metal heating collar 22 is connected via an energy conduit 26 to an energy source 28 for heating the metal heating collar 22. The metal heating collar 22 receives a melt cup 30. The melt cup 30 has upper cylindrical walls 32 and middle conical walls 34 decreasing in diameter until they meet lower cylindrical walls 36. The heating collar 22 and melt cup 30 are sized such that the collar mates with and contacts the upper cylindrical walls 32 of the melt cup. The conical walls 34 and cylindrical walls 36 of the melt cup extend below and do not contact the heating collar 22.

An embodiment of the melt cup 30 is shown in cross-section in FIG. 4. The upper cylindrical, middle conical and lower cylindrical walls 32, 34, 36 are formed at least in part of a nonstick wall 38 preferably made from Teflon®. An outer, heat-conductive metal wall 40, preferably made of aluminum or stainless steel, surrounds and contacts the upper cylindrical walls 32 and an upper portion of the middle conical walls 34. An outer insulative ceramic wall 42 surrounds and contacts the lower portion of the middle conical walls. This outer insulative ceramic wall 42 acts as a barrier to the transfer of heat from the outer heat-conductive wall 40 to the lower cylindrical walls 36 of the melt cup. Preferably the melt cup 30 has a horizontal wall 44 separating the space defined by the middle conical walls 34 and the lower space defined by the cylindrical walls 36. The horizontal wall 44 has a microbore 46 through which the melted clear liquid may be drawn. The thin skin 10 of starting materials is layered on the nonstick surface of the upper cylindrical walls 32 of the melt cup 30.

Referring back to FIG. 3, the device includes a sealing member 48 for closing off the open end of the lower cylindrical walls 36. The sealing member includes a plug 50 sized to sealably fit into the opening of the lower cylindrical walls 36. Preferably the top surface of the plug 50 is a Teflon® or Gortex® filter membrane 52. This filter membrane 52 communicates with passages (not shown) which in turn communicate with a vacuum 54, such that a force indicated by arrows 56 may be applied to pull the melted liquid through the microbore and into the space defined by the lower cylindrical walls 36. This vacuum force aids in collecting the melted liquid and acts to eliminate any bubbles that may be trapped within or below the melted liquid as it collects. This embodiment also includes a cooling device 58 for providing a cooling force indicated by arrows 60 to the lower cylindrical walls 36 of the melt cup 30.

In operation, the melt cup 30 is coated with the skin 10. The melt cup 30 then is inserted into the heating collar 22. The skin then will melt with the clear melt beading and immediately flowing away from the heat to the horizontal wall 44 of the melt cup. The vacuum force then pulls the clear liquid through the microbore into the chamber formed by the horizontal wall 44, plug 50 and the lower cylindrical walls 36 of the melt cup 30. Preferably, the chamber is sized and the amount of pelleting material is selected such that a small excess of melted clear liquid remains above the horizontal wall 44 in communication with the chamber through the microbore 46. It has been discovered that if the material is allowed to cool in the absence of the horizontal wall, a hollow may form centrally of the exposed face of the material. By introducing the horizontal wall with a microbore and using an excess of material communicating with the chamber through the microbore, the hollow does not occur when the material cools. An excess amount of material is not required if the horizontal wall does not contain a microbore and is introduced to cover the material without trapping air only after all the melt has entered the chamber. The clear liquid then cools in this chamber, forming the pellet. The pellet is subsequently removed from the chamber.

Figure 5:
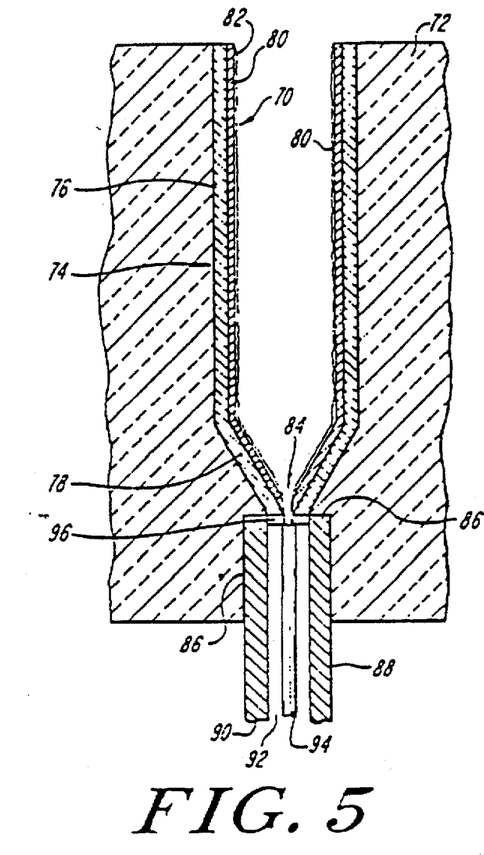
FIG. 5 is a schematic cross-sectional representation of another embodiment of a device for carrying out the invention.

Another embodiment of a device of the invention is shown in cross-section in FIG. 5. In this embodiment, the melt cup 70 is received completely within the ceramic block 72 rather than extending through the ceramic block as in the previous embodiment. A heating collar 74 is contained in the ceramic block 72. The heating collar 74 has upper cylindrical walls 76 and lower conical walls 78 decreasing in diameter. The melt cup 70 has mating walls 80 sized to be received and contact the walls 76, 78 of the heating collar 74. The inside surface 82 of the melt cup 70 is coated with a nonstick surface such as Teflon®.

The conical portion of the mating walls 80 of the melt cup 70 end in an exit port 84 opening into a chamber defined by the chamber-forming walls 86 of the ceramic block 72. The chamber formed by the chamber-forming walls 86 is sized to receive a pellet-forming cylinder 88. The pellet-forming cylinder 88 has outer walls 90 and a central bore 92 through which a plunger 94 may be passed.

In operation, the pellet-forming cylinder 88 is inserted into the chamber defined by the channel-forming walls 86 of the ceramic block 72. The plunger 94 is moved to a closed position such that it closes off the exit port 84 of the melt cup 70. The beads of melted pelleting material will run down the walls of the melt cup 70 and collect forming a pool above the exit port 84 of the melt cup. The plunger then is withdrawn pulling the clear liquid through the exit port 82 of the melt cup into the bore 92 of the pellet-forming cylinder. The liquid is allowed to cool into a pellet within this bore. Preferably, the exit port 84 has a substantially smaller diameter than the diameter of the bore 92. In this manner the desired amount of liquid is drawn into the bore 92 with the excess remaining in the melt cup 70. Once the liquid has cooled and hardened the pellet-forming cylinder is withdrawn from the chamber with the pellet breaking away from the excess of material remaining in the melt cup. The pellet then may be released from the chamber by moving the plunger 94.

Although there is no intention to be bound by any particular theory of the invention, it is believed that the pellet forms without degradation because the melt is motivated from the heat source immediately upon melting and is not overexposed to heat. It has been found that degradation will occur if a melt of starting materials is maintained at about the melt temperature for any extended period of time. Accordingly, it is believed that very high flash temperatures are possible so long as the melt is not maintained at or above the melting temperature but rather is immediately cooled.

It is believed that some of the shortcomings of the prior art are due to overexposing the melt to the melting temperatures. Following the methods of the prior art, the pelleting materials do not melt uniformly but rather melt about the periphery first with melting progressing slowly toward the central region of the packed material. Ostensibly, the material melting first is exposed to heat for an extended period of time until all of the material melts. According to a preferred embodiment, the pelleting materials are in the form of a skin that is thin enough such that the materials will melt approximately simultaneously, in not more than about 10 seconds. The material is then motivated immediately from the source of heat. In this manner, degradation of the pelleting materials is avoided. Preferably the skin is less than about 1 mm in thickness. According to the process of the invention, the starting materials may be exposed to flash temperatures more than twice those indicated in the prior art.

It also is preferable that the conductive wall to which the heat is applied is thin enough such that the material is not slowly heated, but rather is exposed to high temperatures immediately. To insure that the melt is uniform or instantly isotropic, the heat source should completely surround the material to prevent spot melting. According to another embodiment of the invention, the heat may be delivered quickly and uniformly through the thin conductive wall by passing electrical current through the conductive wall. This method is currently preferred and is described in greater detail in Example 3.

There may be no practical limit to the flash temperatures to which the conductive walls are exposed. Higher temperatures, in fact, may expose the material to heat for a shorter time and the material may, therefore, be less likely to degrade.

While desirable results have been achieved using a skin of material, it may be that the same results can be achieved by exposing the pelleting materials to other conditions. For example, a packed pellet of the starting materials possibly may be exposed to microwave conditions to achieve the uniform melt. The important parameters are that the pelleting materials are exposed to the melting conditions for the shortest time possible and that the phase transition from solid to liquid occurs approximately simultaneously for all the material.

The rate at which the melt is cooled may affect the integrity of the pellet. The rate at which the clear melt cools may also affect the structure and the kinetics of release of the pellet. In preliminary experiments, noneutectic melts appeared to crystallize as eutectics initially with the surplus of material spot crystallizing throughout the eutectic lattice. These points of spot crystallization appeared to weaken the overall structure of the crystallized pellet. By subjecting the noneutectic melt to quenching or rapid cooling conditions, the surplus material did not appear to crystallize properly, but rather appeared to solidify amorphously throughout the eutectic lattice. The resulting structure appeared to be more stable and possibly may have better release kinetics than a eutectic melt. Therefore, it appeared desirable to use a noneutectic mixture and apply rapid cooling conditions to the mixture as soon as the melt is collected into a pellet forming chamber. In practice, quenching has not been practical without also causing uneven and premature recrystallization possibly due to the apparatus employed. Currently, the preferred parameters for recrystallization using the apparatus described in Example 3 are heating the funnel connecting with the pellet-forming chamber, and allowing the melted material to recrystallize gradually in an unheated chamber.

A partially fused pellet also may be possible according to the invention. In a partially fused pellet, the starting materials are exposed to conditions such that only the carrier material melts, with the active material remaining as a solid dispersion throughout the melt. When the partial melt solidifies a pellet having clinically desirable drug release kinetics may result. Such partially fused pellets may be useful for the delivery of drugs which are either not steroids or do not have crystalline properties.

EXAMPLE 1

85 grams of pharmaceutical grade, micronized norethindrone (provided by Diosynth, Inc. of Chicago, Ill.) and 15 grams of pure, pharmaceutical grade cholesterol (provided by ICN Pharmaceuticals of Covina, Calif.) were intimately mixed and ground in a mortar and pestle. Thirty-five milligrams of this mixture then were spread on a Teflon®-coated steel spatula. The stainless steel spatula was approximately 20 mm in length and 10 mm in width and was covered uniformly with a thin layer of Teflon® tape. The skin applied was about 0.5 mm in thickness. The nonTeflon® coated side of the spatula then was brought in contact with a hot plate which was heated to approximately 500° F. A clear melt resulted which beaded up like mercury and rolled off the surface of the spatula when the spatula was held at an angle about 45° to horizontal. The spatula was in contact with the hot plate for less than 10 seconds. Upon cooling, the fused material was pure white, implying the lack of degradation products. The absence of any yellow indicated that there was no de-ethynylation of the norethindrone. The pellet was resilient and could be filed and formed with a very gentle abrasive action. Based on a visual light microscopy of the fracture surface, the pellet appeared to have the same characteristics of the very best of those made according to the prior art methods.

EXAMPLE 2

The same procedure as set forth in Example 1 was followed except that the starting materials were applied to the Teflon® coated spatula in the form of a paste. Two grams of the mixture of norethindrone and cholesterol were mixed with 2 ml of 100% laboratory grade ethyl alcohol using a spatula to form a paste. The paste was spread onto the spatula in a thickness of about 0.5 mm and allowed to dry in a vacuum oven for 30 minutes at 60° C. Then the same steps enumerated in Example 1 were followed. The melt occurred about 3–5 seconds after contacting the spatula with the hot plate. The resulting pellet exhibited the same characteristics of the pellet made according to Example 1.

EXAMPLE 3

Micronized Cholesterol/Norethindrone Flash-Melted Pellets (MFm).

Micronized norethindrone was used as a starting material. Pharmaceutical grade, micronized norethindrone (obtained from Dyosinth, Inc. of Chicago, Ill.) and pure pharmaceutical grade cholesterol (obtained from ICN Pharmaceuticals of Covina, Calif.) were combined at a ratio of 85:15% by weight, respectively, intimately mixed and ground in a mortar and pestle. Between 40 and 50 grams of this mixture were weighed into individual vials. Between 0.5 and 1.0 ml of diethylether was combined with the mixture using a Pasteur pipette to form a slurry. This slurry was immediately transferred by a Pasteur pipette to preformed melt cups, the flowable slurry being spread across the surface of the melt cups as a skin.

The melt cups were formed from rectangular sheets of soft, heat-conductive metal, approximately 1¾ inches in length, 1¼ inches in width and 1 mm in thickness. These sheets were given a nonstick surface on one side by applying a ⅞ inch strip of Teflon® tape centrally across the width of the sheets. The tape used was a 1 millimeter thick Teflon® FEP overlay, sold under the tradename of Bytak Overlay, Chemplast, Inc., Wayne, N.J. Then, a melt cup was stamp-molded into the Teflon® coated portion of each of the metal sheets. The melt cup was generally in the shape of a cross-section of a hot air balloon. It included a central depression (about 1/32 inch deep) in the shape of a portion of a sphere (about ¾ inch in diameter) and a radial depression in the shape of a portion of a funnel. The radial depression extended at its wider end from the central depression to an outer edge of the rectangular sheet forming a channel for directing melted material out from the central depression. When material is placed in the melt cup and the entire sheet is disposed at an angle and heated, the material will melt in the central depression and flow immediately via the channel away from the heated surface.

The sheet itself provides a convenient method for heating the material. Electrical conductors may be attached conveniently to the ends of the metal sheets not covered with the non-stick surface. Electrical current then may be passed directly into the sheet to precisely heat the metal of the sheet nearly instantaneously. Likewise, the current can be discontinued to remove the source of heat nearly instantaneously.

One ml of paste was spread onto the central depression of the stamped melt cup. The diethylether was allowed to evaporate out of the paste, the evaporation being assisted by placing the stamped melt cup in a vacuum oven. Once the paste had dried, the stamped melt cup was connected to a source of controlled electrical current and was disposed at an angle over a pellet-forming device consisting essentially of a heated collection funnel connected to an unheated pellet-forming cylinder having a retractable plunger, such as the pellet-forming cylinder shown in FIG. 5. Then, sufficient electrical current was applied to heat the stamped melt cup to 260° C. The mixture of cholesterol and norethindrone melted completely in a few seconds and flowed immediately upon melting from the stamped melt cup into the collection funnel, heated to 190° C. The heating of the funnel prevents premature recrystallization of the melted mixture. The plunger then was withdrawn pulling the clear liquid through the exit port of the funnel and into the bore of a pellet-forming cylinder. The liquid then was allowed to cool into a pellet within the bore of the pellet-forming cylinder with the excess remaining in the collection funnel. Once the liquid had cooled and hardened into a pellet, the pellet-forming cylinder was withdrawn from the collection funnel with the pellet breaking away from the excess of material remaining in the collection funnel. The pellet then was released from the cylinder by moving the plunger.

The cylindrical pellets formed were approximately 6 to 7 millimeters in length and 2.4 millimeters in diameter. Each pellet weighed between 25 and 26 milligrams.

EXAMPLE 4

Pellets were made as described in Example 3 except that crystallized norethindrone was used as a starting material instead of micronized norethindrone. These pellets were given the designation CFm.

EXAMPLE 5

Pellets were formed as described in Example 3 except that pure norethindrone rather than a mixture of norethindrone and cholesterol was used as the starting material. The pellets so formed were given the designation NFm.

EXAMPLE 6

Thin layer chromatography (TLC) was performed on the starting materials and on the pellets of the invention to determine the relative purity of each. (Mass spectrometry and gas chromatography were not used as it was found that these techniques have the potential to cause degradation of the norethindrone.) TLC was performed with Watman fluorescent silica gel 60A (KGF) with a layer thickness of 250 micrometers. Plate size was about 5×10 cms. Samples of the pellets were dissolved in chloroform (10 milligram per mil) and a drop size of 10 microliters was used. The chromatograms were developed with chloroform containing 5 volume-percent methanol. Development time was about 30 minutes. After drying, the plates were first observed under UV and then sprayed with MeOH/H$_2$S)$_4$=7/3 and heated to 100° C. for five minutes.

The chromatograms of cholesterol and norethindrone each revealed a single spot indicating the absence of any impurity. The chromatograms of cholesterol/norethindrone flash melted pellets using either micronized norethindrone (MFm, Example 3) or crystallized norethindrone (CFm, Example 4) exhibited two spots, one corresponding to cholesterol and the other to norethindrone. Degradation products were totally absent. The flash melted pellets made from pure norethindrone and no cholesterol (NFm, Example 5) exhibited only one spot corresponding to norethindrone.

Figure 6:
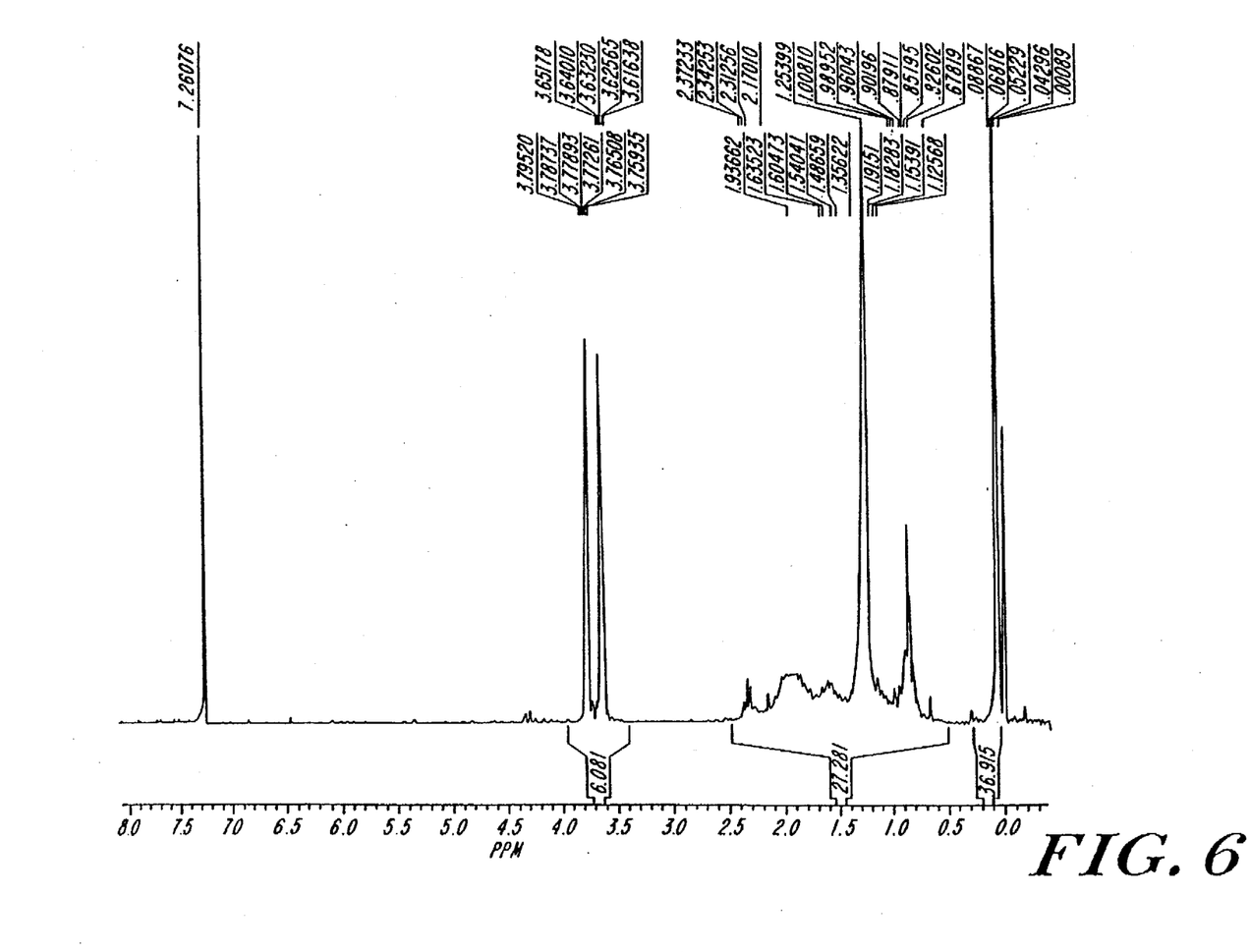
FIG. 6. is the NMR spectra of the impurity caused by overexposing norethindrone to heat.

These results compare favorably to results for pellets formed under conditions characteristic of the processes of the prior art. Heating norethindrone at 260° C. in a sealed container for one minute and allowing the product to cool resulted in a pellet containing an impurity with an RF value of 0.833. The compound having an RF value of 0.833 was isolated and characterized as estrenedione. The NMR 250 MHz$^1$H-NMR spectrum of this compound is shown in FIG. 6. Heating cholesterol at 260° C. in a sealed container for one minute and allowing the product to cool also resulted in a pellet containing an impurity. This impurity had a low RF value (about 0.3).

The MFm, CFm and NFm pellets were also tested to determine whether autoclaving the pellets created any impurities. Pellets were autoclaved at 240° F. for 40 minutes. The chromatograms of these pellets revealed the absence of any impurities. This compares favorably to pellets made according to other methods.

EXAMPLE 7

The in vitro release rates of the pellets made according to Example 3 were determined. The test conditions for this and all other in vitro release studies were as follows. The test pellets were cylindrical, each pellet measuring about 6 millimeters long and 2.4 millimeters in diameter and weighing approximately 25–26 milligrams. Each pellet was placed in an Erlinmeyer flask of 250 ml volume and covered with 100 ml of deionized water. Each flask then was sealed and stored at 37.5° C. in an Eberbach incubator under slight agitation generated by rotary shaking at about 60 rpm. The drug-loaded water was collected and replaced by fresh water approximately every 24 hours. The collected solutions then were analyzed for drug content by their uv absorbence at 240 nm, utilizing a Spectronic 1210 spectrophotometer (Milton Roy Co.).

Figure 7A:
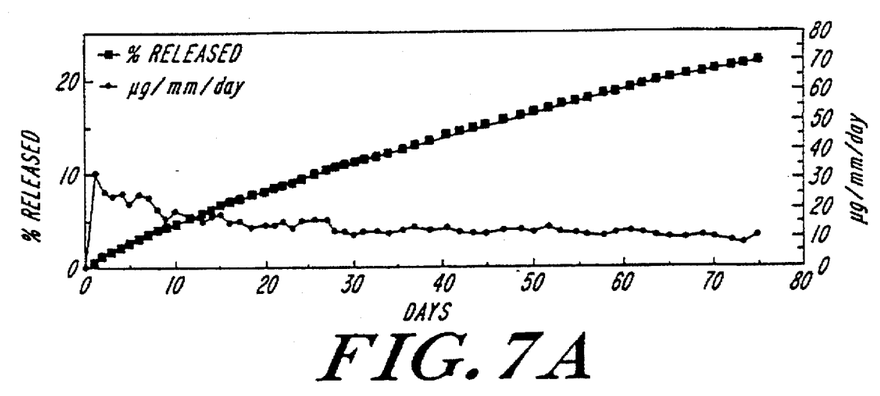
FIGS. 7A and B are graphic representations of the release profiles of flash-melted pellets made from micronized norethindrone and cholesterol.
Figure 7B:
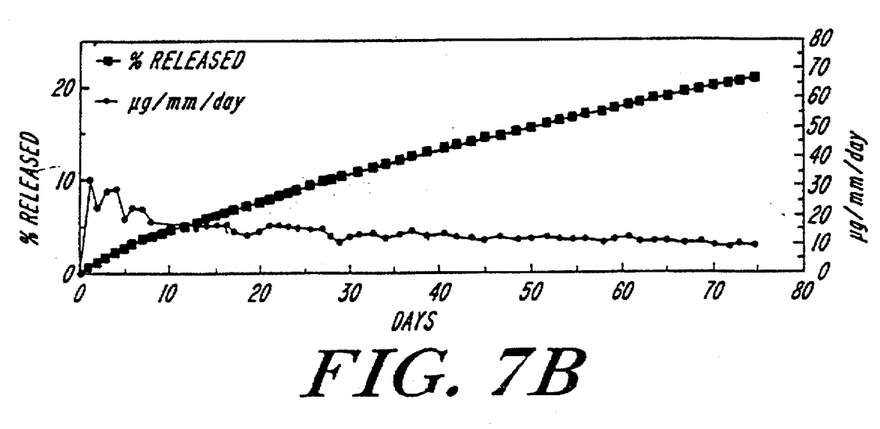
Figure 8A:
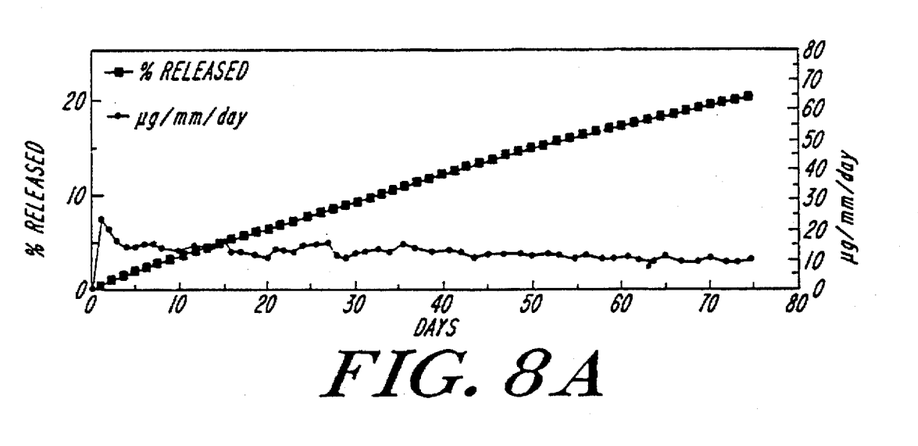
FIGS. 8A and B are graphic representations of the release profiles of the flash-melted pellets of FIG. 7 after autoclaving.
Figure 8B:
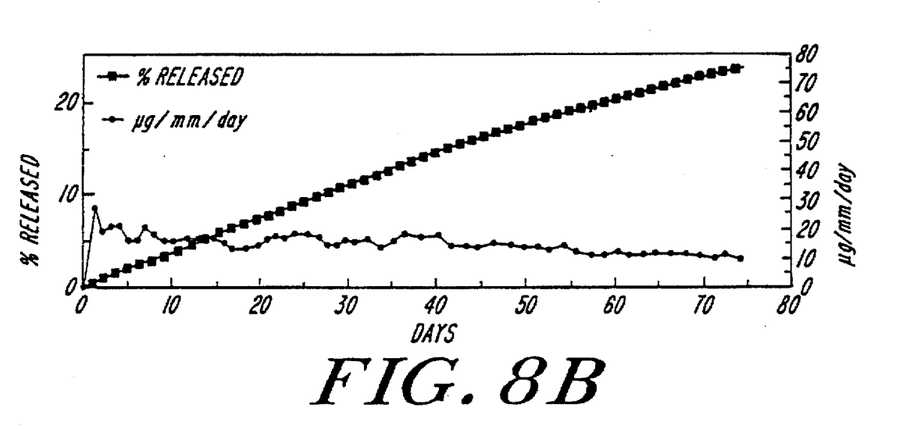

FIGS. 7A and 7B graphically represent the release profiles of cholesterol/norethindrone pellets made from micronized norethindrone and flash melted at 260° C. (MFm). There was an initial elevated level of release for approximately 10 to 15 days. The average release rate calculated for the period from day 30 until day 75 was approximately 11.4 microgram per millimeter per day. When MFm pellets were autoclaved, the release profiles were virtually identical to those of the unautoclaved batch, the average release rate after day 30 being approximately 12.4 micrograms per millimeter per day (FIGS. 8A and B.)

EXAMPLE 8

Figure 9A:
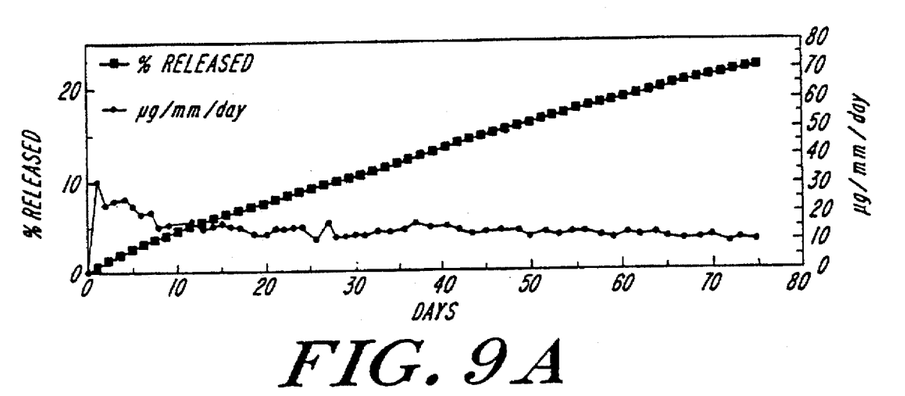
FIGS. 9A and 9B are graphic representations of the release profiles of flash-melted pellets made from crystallized norethindrone and cholesterol.
Figure 9B:
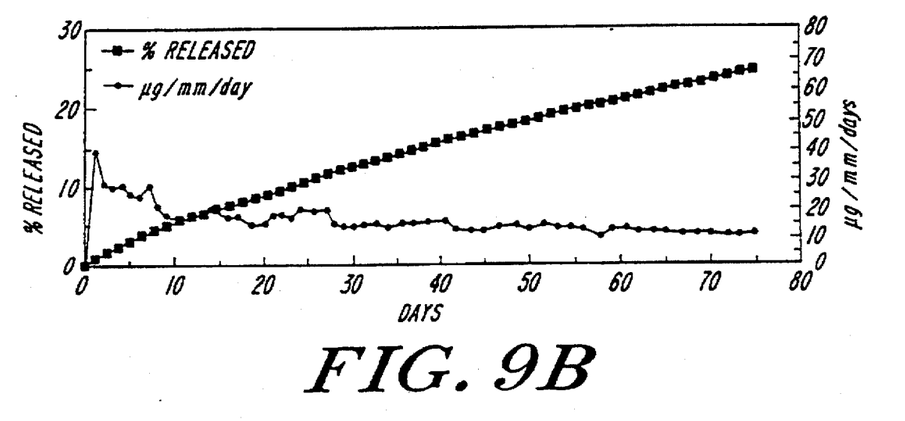
Figure 10A:
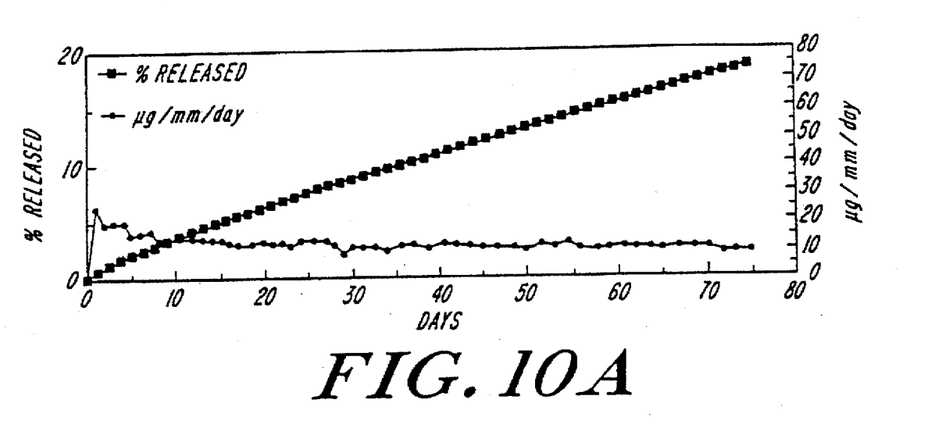
FIGS. 10A and 10B are graphic representations of the release profiles of the flash-melted pellets of FIG. 9 after autoclaving.
Figure 10B:
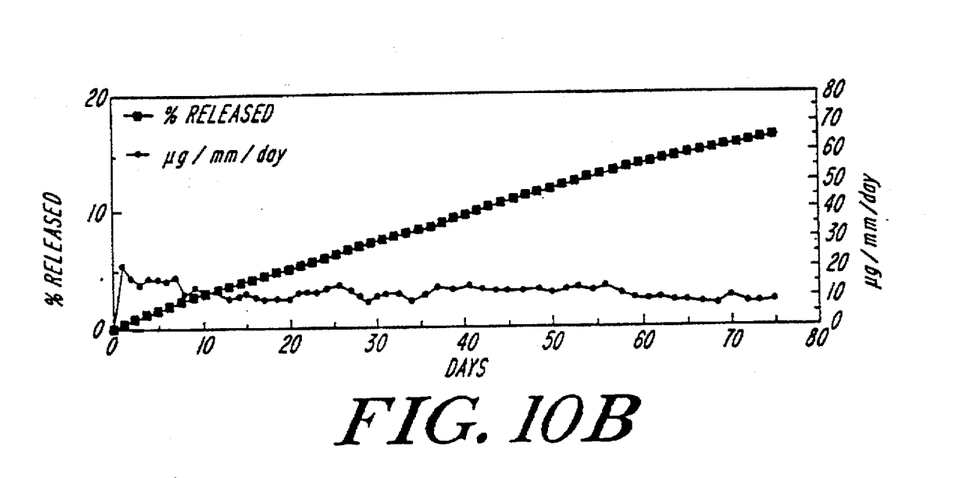

The in vitro release rate of the pellets made according to Example 4 were determined. The release profiles of these cholesterol norethindrone pellets made from crystallized norethindrone and flash melted at 260° C. (CFm) are shown in FIGS. 9A and 9B. After an initial elevated level of release for approximately 15 days, the rate of release stabilized. The average release rate calculated for the period from day 30 to day 75 was approximately 12.7 microgram per millimeter per day. When CFm pellets were autoclaved, the release profiles were somewhat reduced with an average release rate after day 30 of approximately 10.4 micrograms per millimeter per day (FIGS. 10A and B.)

EXAMPLE 9

Figure 11A:
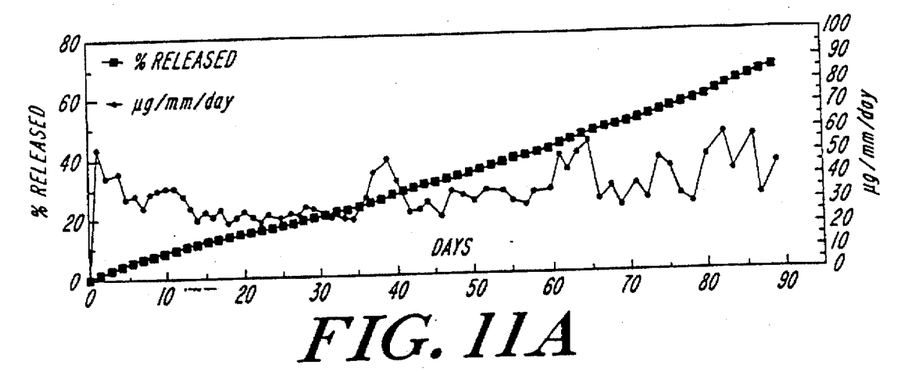
FIGS. 11A–C are graphic representations of the release profiles of flash-melted pellets made from norethindrone only.
Figure 11B:
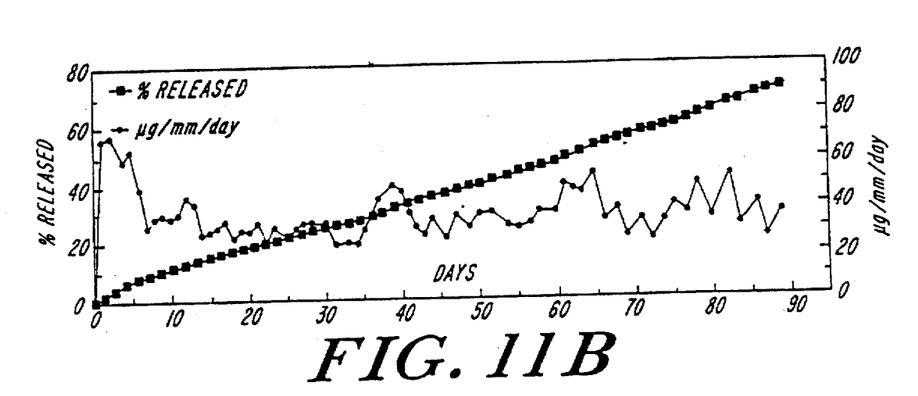
Figure 11C:
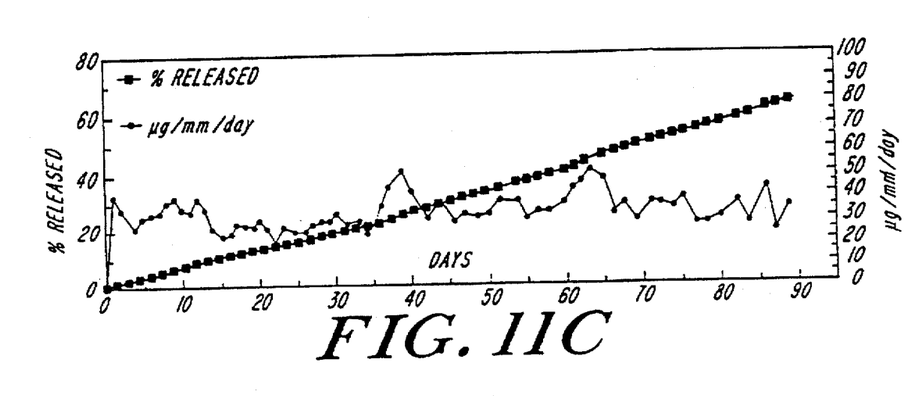

The release profiles of pellets containing only pure norethindrone (NFm, Example 5) are shown in FIGS. 11A–C.

The daily release rates of these pellets were erratic relative to the cholesterol-containing pellets. Daily release ranged from between about 25 and 60 micrograms per millimeter per day.

EXAMPLE 10

Pellets were made as described in Example 3 except that the melt cup was heated to 280° C. instead of 260° C. After an initial elevated level of release for approximately 10 to 15 days, the rate of release stabilized. The average release rate calculated for the period from day 15 to day 90 was approximately 12.2 micrograms per millimeter per day. The summarized data regarding release rates of the three pellets tested are as follows:

TABLE 1

|  | MFm-I | MFm-II | MFm-III |
| --- | --- | --- | --- |
| Minimum | 9.83 | 7.05 | 7.33 |
| Maximum | 18.23 | 17.65 | 15.44 |
| Range | 8.40 | 10.11 | 8.12 |
| Median | 14.24 | 11.49 | 10.98 |
| Mean | 14.00 | 11.38 | 11.23 |
| Std. Error | 0.27 | 0.28 | 0.25 |
| Std. Deviation | 2.00 | 2.05 | 1.78 |
| Variance | 3.98 | 4.21 | 3.18 |
| Coeff. of Variation | 14.26 | 18.03 | 15.89 |

EXAMPLE 11

Pellets were made as described in Example 4 except that the melt cup was heated to 280° C. instead of 260° C. After an initial elevated level of release for approximately 10 to 15 days, the rate of release stabilized. The average release rate calculated for the period from day 15 to day 90 was approximately 9.1 micrograms per millimeter per day. The summarized data regarding release rates of the three pellets tested is as follows:

TABLE 2

|  | CFm-I | CFm-II | CFm-III |
| --- | --- | --- | --- |
| Minimum | 7.18 | 7.08 | 6.66 |
| Maximum | 13.69 | 11.77 | 11.99 |
| Range | 6.51 | 4.68 | 5.33 |
| Median | 9.52 | 8.52 | 9.01 |
| Mean | 9.68 | 8.63 | 8.99 |
| Std. Error | 0.18 | 0.14 | 0.15 |
| Std. Deviation | 1.29 | 1.03 | 1.06 |
| Variance | 1.66 | 1.05 | 1.12 |
| Coeff. of variation | 13.33 | 11.90 | 11.76 |

EXAMPLE 12

The compressional strength of the pellets of examples 3 and 4 was compared to the compressional strength of the pellets as reported by Gupta et al. Gupta et al reported that their pellets crushed under a mean weight of 2.2 kilograms. These weights were distributed along lengths of 6.6 millimeters. Thus, the crush force expressed as kilograms per millimeter is 0.33. The Gupta pellets had a diameter of 2.8 millimeters. The force on a particular pellet is necessarily spread over a region equal to the radial area under that millimeter. Therefore, the force per millimeter of length must be divided by the radial area of the pellet to give an estimate of the tensile strength (kilograms per millimeter cubed). By this calculation, the Gupta pellets had a tensile strength of 0.054 kilograms per millimeter cubed.

Pellets made according to the flash flow methods of the invention had a tensile strength of about 0.128 kilograms per millimeter cubed. This is significant because a fractured pellet implanted under the skin introduces the possibility of migration which negates the reversibility of the method. In general, therefore, the strongest pellet is preferable and clinically safer in subcutaneous drug delivery. Additionally, pellets which are more likely to fracture as they are manufactured or during their loading into injectors introduce increased handling which threatens the sterility and quality assurance of the final product.

EXAMPLE 13

Pellets made according to examples 3, 4 and 5 were investigated by scanning electron microscopy after being broken by applying a radial compression load. The micrographs revealed a surface that was completely crystaline, the existence of particles being absent. The surface was also non-porous. Autoclaving had no effect on porosity.

It should be understood that various changes and modifications of the embodiments described may be made within the scope of this invention. A pellet having a particular size has been described. Other sizes and various shapes are contemplated by this invention. Only a particular active ingredient, norethindrone, and a particular lipoid carrier, cholesterol have been described. Other active ingredients and carriers are contemplated by the invention. For example, cholesteric esters such as cholesterol chloride or cholesterol acetate and derivatives of cholesterol and cholesteric esters may be substituted for pure cholesterol. Other sterols and lipoid carriers other than cholesterol also may be suitable. In fact, as shown in Example 5, the carrier may be eliminated altogether. However, the addition of the carrier stabilizes the release of norethindrone and it should be recognized that other carriers such as fatty acids or neutral fats or well-known emulsifiers and binders such as lecithin may be substituted or added for specific applications.

Steroids other than norethindrone and possibly drugs other than steroids may be substituted as the active component. Also, more than one active steroid drug may be used to form a single pellet. Steroids include, but by no means are limited to, aldosterone, androstane, androstene, androstenedione, androsterone, cholecalciferol, cholestane, cholic acid, corticosterone, cortisol, cortisol acetate, cortisone, cortisone acetate, deoxycorticosterone, digitoxigenin, ergocalciferol, ergosterol, estradiol, 17-α, estradiol-17β, estriol, estrane, estrone, hydrocortisone, lanosterol, lithocholic acid, mestranol, β-methasone, prednisone, pregnane, pregnenolone, progesterone, spironolactone, testosterone, triamcinolone and their derivatives.

It is intended that all matter contained in the above-description or shown in the accompanying drawings shall be interpreted in an illustrative and not limiting sense.

What is claimed is:

1. A totally-fused pellet capable of sustained-release of a steroid drug comprising,
a melted and recrystallized steroid drug free of a carrier combined therewith, said pellet characterized by the absence of thermal degradation impurities caused by overexposing said steroid drug to heat when melting said steroid drug.

2. A totally-fused pellet as claimed in claim 1 further characterized by a break surface that reveals under electron microscopy the absence of discrete particles.

3. A totally-fused pellet as claimed in claim 1 further characterized by a tensile strength of at least 0.1 kilogram/mm$^3$.

4. A totally-fused pellet as claimed in claim 1 further characterized by the continued absence of thermal degradation impurities when autoclaved for 40 minutes at 240° F.

5. A totally-fused pellet as claimed in claim 1 further characterized by an average in vitro release profile of between 10 and 60 micrograms per millimeter length of pellet per day when a cylindrical pellet having a diameter of 2.4 millimeters and weighing about 26 milligrams is placed in an Erlinmeyer flask with daily changes of 100 ml of water at 37.5° C.

6. A totally-fused pellet as claimed in claim 5 further characterized by an in vitro release profile of between 9 and 13 micrograms per millimeter per day.

7. A totally-fused pellet as claimed in claim 5 further characterized by an in vitro release profile having a standard deviation of about 2 micrograms per length of pellet per day or less.

8. A totally-fused pellet as claimed in claim 5 further characterized by an in vitro release profile having a coefficient of variation of less than 20%.

9. A totally-fused pellet as claimed in claim 1 further characterized by an in vitro release profile of about one microgram per square millimeter surface area per day in fresh deionized water.

10. A totally-fused pellet as claimed in claim 1 wherein said steroid drug is norethindrone.

11. A totally-fused pellet as claimed in claim 10 further characterized by a break surface that reveals under electron microscopy the absence of discrete particles.

12. A totally-fused pellet as claimed in claim 10 further characterized by a tensile strength of at least about 0.1 kilogram/mm$^3$.

13. A totally-fused pellet as claimed in claim 10 further characterized by the continued absence of thermal degradation impurities when autoclaved for 40 minutes at 240° F.

14. A totally-fused pellet as claimed in claim 10 further characterized by an average in vitro release profile of between 10 and 60 micrograms per millimeter length of pellet per day when a cylindrical pellet having a diameter of 2.4 millimeters and weighing about 26 milligrams is placed in an Erlinmeyer flask with daily changes of 100 ml of water at 37.5° C.

15. A totally-fused pellet as claimed in claim 14 further characterized by an in vitro release profile of between 9 and 13 micrograms per millimeter per day.

16. A totally-fused pellet as claimed in claim 14 further characterized by an in vitro release profile having a standard deviation of about 2 micrograms per length of pellet per day or less.

17. A totally-fused pellet as claimed in claim 14 further characterized by an in vitro release profile having a coefficient of variation of less than 20%.

18. A totally-fused pellet as claimed in claim 11 wherein said steroid drug is norethindrone, and the pellet is characterized by the absence of detectable thermal degradation products of norethindrone.

19. A pellet capable of sustained release of a steroid drug consisting of a completely melted and recrystallized steroid drug.

20. The pellet of claim 19, wherein said steroid drug is norethindrone.

21. A pellet for sustained release of a drug, said pellet including a completely melted steroid drug free of carrier combined therewith, said pellet produced by:

isotropically melting asteroid drug to form a liquid under conditions in which phase transition from solid to liquid occurs simultaneously for all material in said pellet; and cooling said melted drug to allow recrystallization thereof, said pellet characterized by the absence of thermal degradation impurities caused by overexposing said steroid drug to heat.

22. The pellet of claim 21, capable of releasing said steroid drug into water for a period of about 90 days of an average release rate of about 2–6 micrograms/mm$^2$ per day.

23. A pellet for sustained release of a drug, said pellet comprising 85% by weight norethindrone and 15% by weight cholesterol, the pellet produced by:

isotropically melting said norethindrone and cholesterol to form a liquid in which phase transition from solid to liquid occurs simultaneously for all material in the pellet; and cooling said melted norethindrone and cholesterol to allow simultaneous recrystallization thereof to form a fused matrix, said pellet characterized by absence of thermal degradation impurities caused by overexposing said norethindrone to heat.

24. The pellet of claim 23, wherein said pellet has a tensile strength of at least about 0.1 kilograms/mm$^3$.

* * * * *